ic Patent
Tilley

[11] 4,016,144
[45] Apr. 5, 1977

[54] PREPARATION OF POLYAMIDE FROM OLIGOMERIC POLY-N-CARBOXYLIC ANHYDRIDE

[75] Inventor: James N. Tilley, Cheshire, Conn.

[73] Assignee: The Upjohn Company, Kalamazoo, Mich.

[22] Filed: Sept. 5, 1975

[21] Appl. No.: 610,742

Related U.S. Application Data

[62] Division of Ser. No. 508,990, Sept. 25, 1974, Pat. No. 3,922,295.

[52] U.S. Cl. .................... 260/78 R; 260/77.5 C; 260/77.5 CA; 260/858
[51] Int. Cl.² ............... C08G 18/10; C08G 69/00
[58] Field of Search .................. 260/78 R, 77.5

[56] References Cited

UNITED STATES PATENTS 2,268,586  1/1942  Gilman ........................ 260/78 R
3,642,715  2/1972  Allard ......................... 260/78 R Primary Examiner—Harold D. Anderson
Attorney, Agent, or Firm—James S. Rose; Denis A. Firth

[57] ABSTRACT

Novel oligomeric poly N-carboxylic anhydrides having the following structure are disclosed.

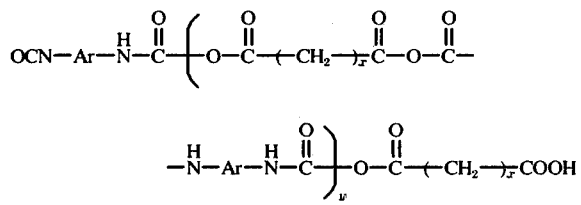

The unit Ar represents arylene and x represents an integer from 1 to 10 and y represents a number having an average value from 0 to 4. The polyanhydrides serve as useful storage stable intermediates for the production of polyamides to which they are easily converted by the elimination of carbon dioxide. A process for the preparation of the polyanhydrides from arylene diisocyanates and α,ω-alkylene dicarboxylic acids is disclosed. Processes for the conversion of the polyanhydrides to the corresponding polyamides are also disclosed.

10 Claims, No Drawings

PREPARATION OF POLYAMIDE FROM OLIGOMERIC POLY-N-CARBOXYLIC ANHYDRIDE

CROSS REFERENCE TO RELATED APPLICATION

This application is a division of copending application Ser. No. 508,990 filed Sept. 25, 1974, now U.S. Pat. No. 3,922,295.

BACKGROUND OF THE INVENTION

1. Field of the Invention

This invention relates to the preparation of polyamides and intermediates thereto, and is more particularly concerned with novel oligomeric intermediates, which are readily converted to polyamides, and with the preparation of said oligomeric intermediates.

2. Description of the Prior Art

Polyamides and copolyamides of many diverse types have been recognized and utilized in the polymer art for many years. Beginning with the pioneer work of Carothers (see U.S. Pat. Nos. 2,071,250, 2,071,251, and 2,071,253) and continuing up to recent technology (see Encyclopedia of Polymer Sci. and Technology, Vol. 10, pp. 347–615, 1969, John Wiley & Sons, New York, N.Y.,) many polyamide compositions have been disclosed. The prior art discloses a variety of methods for preparing polyamides including the melt condensation technique (see U.S. Pat. No. 3,651,022) of a diamine with a dicarboxylic acid; the amine-salt technique (see Preparative Methods of Polymer Chemistry, W. R. Sorenson, et al., p. 62, 1961, Interscience Pub. Inc., New York, New York) wherein the diamine and diacid are prereacted to form the crystalline amine-carboxylate salt prior to polymerization; the reaction of a diamine with a diacid chloride (see U.S. Pat. No. 3,063,966); and the reaction of a diisocyanate with a diacid (see U.S. Pat. No. 3,642,715). While all the methods referred to hereinabove provide polyamides and copolyamides in good yield, purity and molecular weight, they do not provide for any type of prepolymer technology and the advantages to be derived therefrom.

I have now found a novel class of oligomeric poly[α,ω-dicarboxyalkylene-N,N'-dicarboxy(-diaminoarylene)-anhydrides] which are easily prepared and storage stable. These novel oligomers serve as prepolymers for the formation of the corresponding poly or copolyamides by the evolution of carbon dioxide. Further, this method of preparing polyamides provides a technique for obtaining easily other types of polymers such as polyurethanes, polyureas, polycarbodiimides, etc., copolymerized with the polyamides, which method has not been available heretofore using any of the prior art methods.

SUMMARY OF THE INVENTION

This invention comprises oligomeric poly N-carboxylic anhydrides having the structure

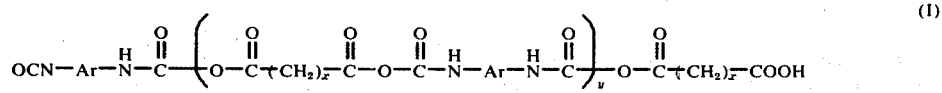

wherein Ar represents an arylene radical, x represents an integer from 1 to 10, and y represents a number having an average value from 0 to 4 inclusive.

The invention also comprises a process for the preparation of oligomeric poly N-carboxylic anhydrides having the structure set forth hereinabove and their conversion to the corresponding polyamides.

The term "arylene" represents a radical obtained by removing two nuclear hydrogen atoms from an aromatic hydrocarbon, and is inclusive of phenylene, tolylene, xylylene, naphthylene, diphenylylene, and compounds having the formula

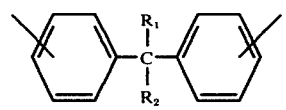

wherein $R_1$ and $R_2$ each represent a moiety selected from the class consisting of hydrogen and lower-alkyl having from 1 to 4 carbon atoms inclusive, such as methyl, ethyl, propyl, and butyl.

DETAILED DESCRIPTION OF THE INVENTION

It is an object of the present invention to prepare oligomeric poly[α,ω-dicarboxyalkylene-N,N'-dicarboxy(diaminoarylene) anhydrides], hereinafter called poly N-carboxylic anhydrides, or PNCAs for the sake of brevity. Kricheldorf (Die Makromolekulare Chemie 149 (1971), 127–133) has reported the formation of PNCA polymers from isocyanatobenzoic acids and observed "expectedly small" thermal stabilities therein.

The oligomeric PNCA materials having the structure (I) are prepared according to the equation

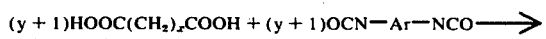

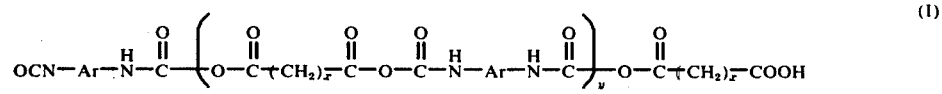

wherein Ar, x and y have the significance as defined hereinbefore. The appropriate dicarboxylic acid and diisocyanate are brought together under anhydrous conditions to form the oligomeric structure (I). The reaction is carried out either in the presence or absence of solvent and over a relatively broad temperature range which will be set forth in detail hereinbelow. Generally speaking, the lower temperatures are employed when a solvent is present which is a preferred embodiment of the present invention. The diisocyanate is added to a solution of the dicarboxylic acid over a period of time and the PNCA product is isolated by standard methods known to those skilled in the art, such as vacuum stripping of the solvent, or filtration, or precipitation by the addition of a second solvent. When the PNCA materials are prepared in the absence of solvent, at higher reaction temperatures, it will be obvious to those skilled in the art that reaction times will be shorter than when the preparation is carried out in solvent.

Surprisingly and unexpectedly the PNCA products are characterized by having a remarkable degree of thermal stability. Illustratively, the isolated oligomeric PNCA compounds display little or no change upon heating up to 100° C and only minimal changes up to 150° C. In a further unexpected finding the PNCA polymers having structure (I) only form oligomers and do not form true polymers. It will be recognized by one skilled in the polymer art that an oligomer is a polymer consisting of only a few monomer units such as a dimer, trimer, tetramer, etc., and up to a limit of about ten repeat units. It will be further recognized that the oligomeric product obtained represents an average of a mixture of the dimer, trimer, tetramer, etc. The average number of repeat units is defined as the number average degree of polymerization (D.P.) and for simple difunctional reactants in polycondensation polymerizations it is obtained from the expression $$D.P. = 1/1-p$$

wherein $p$ is the extent of reaction expressed as a fraction. (see Textbook of Polymer Sci., F. W. Billmeyer, p. 265–266, 1971, John Wiley & Sons, Inc., New York, N.Y.)

The extent of reaction for the formation of (I) is readily determined by any suitable analytical method used for end-group analysis. A particularly suitable method is infrared analysis (see Handbook of Industrial I. R. Analysis, p. 253 by R. G. White, Plenum Press, 1964, New York). It is readily apparent from the formula (I) that both isocyanate (—NCO) and carboxylic acid (—COOH) end groups are present and the NCO functional absorption band at $4.4\mu$ is particularly suited for such analysis. The degree of polymerization of structure (I) as determined from infrared analyses for unreacted NCO is from about 2 to about 10, so that the value of y therefore will be from about 0 to about 4. The PNCA products are obtained either as free flowing powders when prepared in solvent, or as a glassy solid in the absence of solvent.

In a preferred embodiment of the present invention the proportions of diisocyanate to dicarboxylic acid are advantageously from about 1.0 mole to about 1.10 mole and preferably from about 1.0 mole to about 1.01 mole respectively. The proportions of reactants set forth above provide the PNCA oligomers having approximately equivalent end-group concentrations of free isocyanate and carboxylic acid groups. In yet another embodiment the diisocyanate is used in excess to provide an isocyanate rich oligomer. Such oligomers find particular uses and have advantages to be discussed hereinbelow. The proportions of reactants to be employed in this embodiment are advantageously from about 2 moles to about 1.0 mole and preferably from about 1.5 moles to about 1.0 mole of diisocyanate to diacid respectively.

Typical examples of the a,w alklenedicarboxylic acids employed in the present invention are malonic acid, succinic acid, glutaric acid, adipic acid, pimelic acid, suberic acid, azelaic acid, sebacic acid, 1,11-undecanedioic acid, 1,12-dodecanedioic acid and mixtures of these. A preferred class of acids consists of: adipic acid, pimelic acid, suberic acid, azelaic acid, sebacic acid, 1,11-undecanedioic acid, 1,12-dodecanedioic. A particularly preferred acid is azelaic acid.

The diisocyanates employed in the present invention are compounds having the structure, $Ar(NCO)_2$, wherein the radical, Ar is defined hereinabove. Illustrative examples are, m-phenylenediisocyanate, p-phenylenediisocyanate, 1,5-napthalenediisocyanate, biphenyl-4,4'-diisocyanate, 4,4'-methylenebis(phenylisocyanate), 2,4-toluenediisocyanate, 2,6-toluenediisocyanate, and mixtures thereof. A particularly preferred class consists of 4,4-methylenebis(phenylisocyanate), 2,4-, and 2,6-toluenediisocyanates, and mixtures thereof.

In one embodiment of the present invention the reactants as set forth hereinabove are brought together during stirring in the absence of solvent. Accordingly, the reactants are heated from about 80° to about 150° C and preferably from about 90° to about 120° C. The duration of heating is from 0.5 minute to about 30 minutes and preferably from about 4 minutes to about 8 minutes.

In a preferred embodiment the reactants are brought together in a non-reactive polar solvent. Illustrative of such solvents are; N,N-dimethylacetamide, N,N-dimethylformamide, N-methyl-2-pyrrolidone, hexamethylphosphoramide, dimethylsulfoxide, tetrahydrofuran, and the like. The concentration of reactants dissolved in the solvent is not critical and can vary from about 1 percent to about 40 percent by weight. A particularly preferred group of solvents consists of N-methylpyrrolidone and tetrahydrofuran. The reaction temperature is advantageously from about −60° to about 50° C and preferably from about −40° C to about 25° C. The time of reaction will vary according to the temperature and the solvent but is generally from about 10 minutes to about 6 hours and preferably from about 30 minutes to about 4 hours.

The extent of the oligomer formation during the course of the polymerization, whether carried out in solvent or as a melt as described hereinabove, is easily monitored by infrared absorption analysis already described. In addition, the final oligomeric PNCA is analyzed in like fashion.

It is yet a further object of the present invention to prepare polyamides of high molecular weight having the structure (II) from the PNCA oligomers of structure (I) by heating said oligomers so as to remove carbon dioxide according to the equation

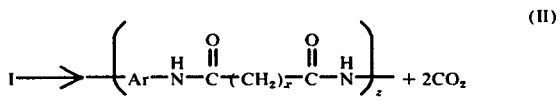

Ar and x have the significance defined hereinbefore, and z represents the degree of polymerization associated with high molecular weight polyamides.

The poly N-carboxylic anhydrides having structure (I) can be prepared either in a melt reaction or in solvent as set forth in detail hereinbefore and then converted directly to the polyamide without isolation of (I). Alternatively, the compounds of structure (I) can be isolated and later transformed, either in the presence or absence of solvent, into the corresponding polyamide (II). Accordingly, the most preferred method will be dictated by the application, or end-use of the final polymer system. In a further embodiment, the polymerization of the PNCA to polyamide is catalyzed by the presence of a tertiary amine, where, in its most preferred embodiment, a solvent is employed thereby facilitating the separation of the final polyamide from the catalyst.

The tertiary amine catalyst employed can be any of the aliphatic, or cycloaliphatic amines normally used in processes which call for tertiary amine catalysts. Examples of such amines include: triethylamine, tributylamine, triethylenediamine, N-ethylmorpholine, N-methylmorpholine, N,N-dimethylcyclohexylamine, pentamethyldiethylenetriamine, and the like. A particularly preferred amine is triethylamine. The concentration of amine catalyst employed is advantageously from about 0.5 weight percent to about 100 weight percent and preferably from about 2 weight percent to about 20 weight percent based on starting PNCA.

When the PNCA is converted to polyamide in the absence of solvent, the oligomer, either in the form of a powder or a pulverized form of the glassy material, is heated at about 160° to about 325° C and preferably at about 160° to about 300° C for about 0.5 hour to about 10 hours.

In a preferred embodiment the PNCA (I) is dissolved in a solvent of the type, and at a concentration as recited hereinbefore. In addition a tertiary amine of the type and in the concentration set forth above, is added whereupon the solution is heated at about 80° to about 200° C, and preferably from about 90° to about 150° C, for a period of time from about 2 hours to about 24 hours and preferably from about 5 hours to about 15 hours. Purification of the polyamide is carried out by employing standard techniques of precipitation and washing known to those skilled in the polymer art. The polyamide is obtained in high yield and good molecular weight.

The various embodiments of the present invention pertaining to the formation of polyamides or copolyamides from the oligomeric PNCA materials, can be carried out in the presence of other monomers or polymer systems. The monomers or polymer systems can be either reactive with the PNCA end groups, or alternatively non-reactive. In the former embodiment a copolymer consisting of the polyamide and the other polymer is obtained.

In the non-reactive case a physical mixture of the two polymers is obtained. As a further example, a PNCA oligomer prepared from excess diisocyanate as referred to hereinabove is easily reacted with a urethane prepolymer having hydroxyl end-groups equivalent to the excess of isocyanate, in a solvent such as those previously described. The PNCA is then converted to polyamide according to the teachings of the present invention. The resulting block copolymer consists of polyamide blocks linked to polyurethane blocks. Similarly, an amine terminated urethane prepolymer gives rise to a copolymer having polyamide and polyurethane blocks joined by urea linkages. In like fashion a polycarbodiimide can be copolymerized with the NCO rich oligomer in the presence of any of the carbodiimide catalysts known to those skilled in the art. After conversion the resulting copolymer consists of polycarbodiimide blocks and polyamide blocks. In yet a further adaptation of the NCO rich oligomers the PNCA can be reacted with any of the diols known to those skilled in the polyurethane art. After conversion, the polymer contains polyamide blocks joined by urethane linkages.

The oligomeric poly N-carboxylic anhydride products of the present invention find particular utility as intermediates in the preparation of polyamides or copolyamides. This aspect of their utility is particularly enchanced by the fact that, as intermediates, they provide for the formation of block copolymers consisting of polyamide blocks and other other blocks such as polyurethane, polyurea, and polycarbodiimide. Thusly they provide in some cases, a means for preparing copolymers which are otherwise difficult if not impossible to obtain. As a further aspect of their utility, the oligomers of the present invention are useful in the facile in situ preparation of polyamides within another environment such as in baked-on coatings and enamels. In yet a further aspect of their utility the compounds of the present invention are useful as agents for conferring either heat resistance or fire resistance to another system by virtue of their thermal conversion to polyamides which are known to possess heat and fire resistant properties and by the evolution of non-flammable carbon dioxide. A particularly advantageous utility in this respect is their use in intumescent coatings. Such coatings find wide application as thermal and fire resistant coatings for rocket nose cones, building panels, tanks, pipe lines and the like.

The polyamide products derived from the process of the present invention possess the well known and widely diversified uses for which polyamides are well recognized. Examples of such uses include fibers, films, moldings, castings, and extrusions which encompass a myriad of applications ranging from very small parts to very large ones. In the form of fibers, the polyamides are useful in the fabrication of curtains, carpets, tires, conveyor belts, rope, etc. As film they are useful, for example, as lining for electrical components. As castings and moldings they find use as gear wheels, electrical component parts, appliance parts, etc.

The following preparations and examples describe the manner and process of making and using the invention and set forth the best mode contemplated by the inventors of carrying out the invention but are not to be construed as limiting.

EXAMPLE 1

A 100 ml. three-neck flask which was thoroughly dried was equipped with a stirrer, thermometer, gas in-let tube, and an additional funnel. The flask was charged with 3.8040 g. (0.0202 mole) of azelaic acid and the reaction system maintained under a blanket of oxygen-free nitrogen in order to exclude air and atmospheric moisture. Twenty-five ml. of tetrahydrofuran was added and the azelaic acid dissolved during stirring. A solution consisting of 5.0280 g. (0.0201 mole) of 4,4'-methylenebis(phenylisocyanate) dissolved in 3.6 g. of tetrahydrofuran was prepared separately and charged to the addition funnel. The diisocyanate solution was added to the flask during stirring over a period of 15 minutes at 24°–25° C. The solution was stirred and cooled from 25° C down to −40° C over a period of 4 hours and remained clear and fluid. The solution was stripped under a vacuum of 20–25 mm pressure at 0° C. A white solid was obtained in theoretical yield and further dried at 70°–80° C under 1 mm.

An infrared spectrum of a KBr pellet of the product displayed the absorption band at 5.57μ for the mixed anhydride and the 4.40μ and 5.75μ bands for the isocyanate and carboxylic acid end groups respectively.

The unreacted isocyanate was 14 percent and was determined using standard methods of I. R. analysis based on the NCO band (see Handbook of Industrial I. R. Analysis, p. 253 by R. G. White, Plenum Press, New York, 1964). The number average degree of polymerization as calculated from the extent of isocyanate reaction was approximately 8. The oligomeric poly N-carboxylic anhydride melted at 265°–270° C with frothing and corresponded to the following structure.

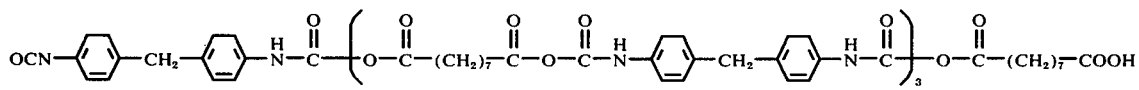

An infrared scan of the polymer after storage for at least 6 months in the cold (approximately 0° C) showed no appreciable change.

EXAMPLE 2

A 100 ml. three-neck flask equipped as described in Example 1 was charged with 3.8204 g. (0.0203 mole) of azelaic acid and dissolved in 25 ml. of dry N-methylpyrrolidone (NMP). The addition funnel was charged with a solution of 5.0280 g. (0.0201 mole) of 4,4'-methylenebis(phenylisocyanate) dissolved in 3.7 g. of NMP. The isocyanate was added to the flask over a period of 11 minutes while the reaction mixture was cooled to −12° to −18° C. No carbon dioxide evolved during the addition. Stirring was continued for 24 minutes at a reaction temperature of −15° to −21° C during which time the flask contents became viscous and a thick residue formed. Following this, a total of 0.55 ml. of triethylamine was slowly added over a 45 minute period at a temperature of −5° to −25° C. No gas evolution was observed and the reaction mixture remained fluid but viscous throughout. The reaction mixture was allowed to return to ambient temperature while it was left standing overnight. The flask contents formed into a brittle glass which was easily pulverized. The infrared scan of this material showed the characteristic mixed anhydride absorption around 5.6μ.

The pulverized material, which contained the NMP, was then heated and stirred for a period of about 13 hours at a pot temperature of 90°–140° C. The flask contents began to agglomerate and eventually became gelatinous. A solid was precipitated by stirring the product into 800 ml. of water. It was washed with two 400 ml. portions of water, followed by two 250 ml. portions of methanol. It was dried overnight at 140° C under 0.5 mm. pressure and provided 5.95 g. (84.5% yield) of poly[4,4'-methylenebis (phenyl) azelamide]; ηinh(0.5% in $H_2SO_4$)=1.2; infrared spectrum identical to authentic polyamide.*

*Prepared from reaction of 4,4'-methylenedianiline with azelaoyl chloride in solution. See "Condensation Polymers", Chapter IV by P. W. Morgan, 1965, Interscience Publishers, New York.

EXAMPLE 3

A sample of the oligomeric poly N-carboxylic anhydride (PNCA) as prepared in Example 1 was converted to poly[4,4'-methylenebis(phenyl)azelamide] by heating in a duPont 900 Thermal Analyzer instrument equipped with the duPont Thermal Gravimetric Analysis (TGA) 950 Unit.

A differential thermal analysis (DTA) scan was determined for the oligomer using the duPont 900 Thermal Analyzer instrument, under $N_2$ at a rate of 20 deg./min. The sample was cooled and rerun at the same rate. Comparative DTA scans were also obtained for virgin authentic poly[4,4'-methylenebis(phenyl)azelamide] and on the cooled and rerun sample. The correspondence of the thermal events in the scans between the polyamide formed from PNCA as it was heated during the DTA scan and authentic polyamide is set forth in Table I. The profiles of heated or annealed samples were characterized by having more complicated thermal events occurring during heating.

TABLE I

DTA Comparison of Poly[4,4'-methylenebis(phenyl)azelamide] with Authentic Polymer.

| | Sample | | Authentic* polyamide |
|---|---|---|---|
| Virgin Polymer | m.p. (° C) | 250–280 | 250–280 |
| | Cool (recryst.) (° C) | 245 | 235 |
| Annealed or heat treated polymer | Endothermic Event (° C) | 230–245 | 225–255 |
| | Exothermic Event (° C) | 245–250 | 255–260 |
| | m.p. (° C) | 260–275 | 270–285 |

*The identical complex DTA pattern for poly[4,4'-methylenebis(phenyl)azelamide] has been observed by D. A. Holmer, et al., J. Polymer Sci[5]1547 (1972).

Table II sets forth the weight loss of the polyanhydride during its conversion to polyamide and the corresponding percent conversion thereto. The theoretical weight loss due to $CO_2$ evolution when the polyanhydride has been completely converted to polyamide is 20.1%. The sample was heated at 15° C per minute under nitrogen and the instrument suppression was varied so that the maximum sensitivity was at the beginning of the heating cycle when weight loss was smallest.

Table III sets forth a comparison of the TGA of a sample of the polyamide after its formation and continued heating, with the TGA of authentic polyamide and the correspondence between the two samples is evident. The discrepancy in the 450° to 500° C range is considered an artifact.

TABLE II

Wt. Loss During Thermal Conversion of PNCA to Polyamide.

| Temp. (° C) | Wt. Loss (%) | Percent Conversion to Polyamide |
|---|---|---|
| 50 | 0 | 0.0 |
| 100 | 0.10 | 0.5 |
| 150 | 3.7 | 18.4 |

TABLE II-continued

Wt. Loss During Thermal Conversion of PNCA to Polyamide.

| Temp. (° C) | Wt. Loss (%) | Percent Conversion to Polyamide | | |
|---|---|---|---|---|
| 200 | 7.0 | 34.8 | | |
| 250 | 13.5 | 67.2 | | |
| 265 | 15.5 | 77.0 visual melt range | DTA melt range | |
| 270 | 16.2 | 80.6 | | |
| 280 | 17.2 | 85.6 | | |
| 300 | 18.2 | 91.0 | | |
| 350 | 20.3 | 105 | | |
| 400 | 21.2 | | | |
| 450 | 27.7 | | | |
| 500 | 63.0 | | | |

TABLE III

TGA Comparison of Formed Polyamide with Authentic Polymer.

| | Wt. Loss (%) | |
|---|---|---|
| Temp. (° C) | Polyamide | Authentic Material |
| 350 | 0.2 | 0.1 |
| 400 | 1.6 | 1.8 |
| 450 | 9.9 | 29.0 |
| 500 | 55.9 | 85.6 |
| 550 | 85.8 | 89.8 |
| 600 | 89.7 | 90.2 |
| 650 | 98.7 | 97 |
| 700 | 100 | 100 |

EXAMPLE 4

A small polypropylene beaker was charged with 11.4120 g. (0.0607 mole) of azelaic acid, and 2.0898 g. (0.0120 mole) of 2,4-toluene diisocyanate. The beaker and contents were preheated (while covered) for 10 minutes in an oven at 95° – 100° C. Thereupon 12.0672 g. (0.0482 mole) of 4,4'-methylenebis(phenylisocyanate) was weighed in and a semi-micro resin kettle top quickly affixed to the beaker. The top was equipped with a mechanical stirrer and a thermocouple for continuous temperature measurement within the reaction mixture. The beaker was suspended in an oil bath and heated and stirred at a bath temperature of 100° C. The reaction mixture was held for 5½ minutes at a mix temperature of 95° C whereupon a water-white homogeneous phase was formed which foamed slightly then collasped to a gel. It was cooled to form a glassy blend and the infrared analysis displayed the typical mixed anhydride pattern with the 5.6μ absorption which characterizes the poly N-carboxylic anhydride structure, in combination with the isocyanate and carboxylic acid end group absorptions at 4.40μ and 5.80μ respectively. The following data sets forth the TGA analysis of the product and the equivalent percent conversion to the corresponding copoly[4,4'-methylenebis(phenyl)2,4-tolyl azelamide] as the material was heated (assuming theoretical wt. loss due to $CO_2$ evolution as 20.1%. After approximately 400° C the wt. loss was due to thermal degradation of the formed copolyamide.

| Temp. ° C | % Wt. Loss | % Conversion to Copolyamide |
|---|---|---|
| 50 | 0 | 0 |
| 100 | 0.1 | 0.5 |
| 150 | 1.7 | 8.2 |
| 200 | 6.6 | 31.7 |
| 250 | 15.3 | 73.4 |
| 300 | 17.3 | 82.0 |
| 350 | 18.3 | 88 |
| 400 | 19.7 | 94.5 |
| 450 | 30 | — |
| 500 | 84 | — |

The polyamide obtained had the following structure

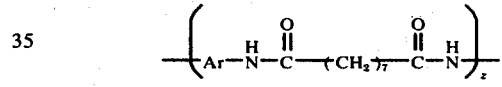

wherein 80 percent of the radicals Ar were

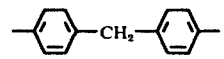

and the remaining 20 percent were

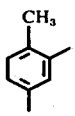

EXAMPLES 5 – 10

The PNCA oligomers set forth in the following Table IV were prepared using the apparatus and procedure set forth in Example 1. The 0.0202 mole of azelaic acid and 0.0201 mole of 4,4'-methylenebis(phenylisocyanate) of Example 1 were replaced by the equivalent amounts of α,ω-alkylenedicarboxylic acids and diisocyanate as indicated hereinbelow. The oligomers had the following structure

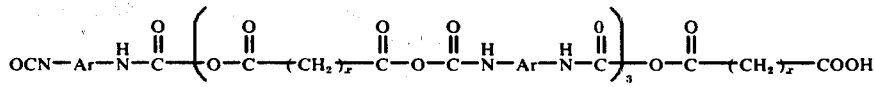

TABLE IV

PNCA Oligomers

| Example | Diacid | Diisocyanate | x | Ar | I.R. Analysis |
|---|---|---|---|---|---|
| 5 | succinic | 4,4-methylenebis(phenylisocyanate) | 2 | 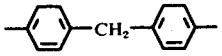 | 5.6μ (mixed anhydride) |
| 6 | adipic | 4,4-methylenebis(phenylisocyanate) | 4 | 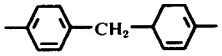 | 5.6μ (mixed anhydride) |
| 7 | sebacic | 4,4-methylenebis(phenylisocyanate) | 8 | 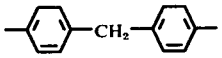 | 5.6μ (mixed anhydride) |
| 8 | 1,12-dodecanedioic | 4,4-methylenebis(phenylisocyanate) | 10 | 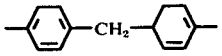 | 5.6μ (mixed anhydride) |
| 9 | adipic | 2,4-toluenediisocyanate | 4 | 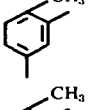 | 5.6μ (mixed anhydride) |
| 10 | 1,12-dodecanedioic | 2,4-toluenediisocyanate | 10 | 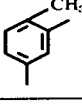 | 5.6μ (mixed anhydride) |

The oligomers were converted to the corresponding polyamides using the procedure set forth in Example 2. The N-methylpyrrolidone semi-solid solutions (about 25 percent by weight of PNCA) of each oligomer were heated at 125° C for 12 hours. The corresponding polyamides were obtained by precipitation into 800 ml. of water, collected and washed with two 400 ml. portions of water, followed by two 250 ml. portions of methanol. The polyamides were dried overnight at 140° C under 0.5 mm pressure to yield light cream colored powders. The infrared absorption spectrum of each polyamide was identical to the spectrum of the authentic polymer.

I claim:

1. A process for converting an oligomeric poly N-carboxylic anhydride consisting essentially of

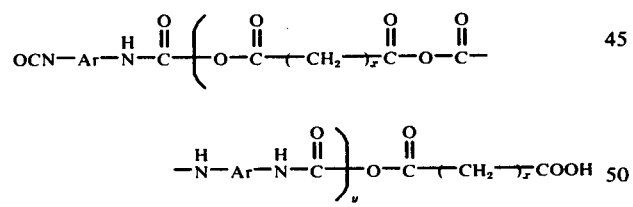

wherein Ar represents an arylene radical, x represents an integer from 1 to 10, and y represents a number having an average value from 0 to 4 inclusive into a film forming polyamide having the recurring unit

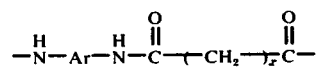

wherein Ar and x are as defined hereinabove said process comprising heating said oligomeric poly N-carboxylic anhydride at a temperature of from about 80° to about 325° C so as to remove carbon dioxide.

2. A process according to claim 1 wherein Ar represents the radical

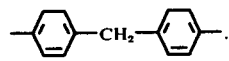

3. A process according to claim 1 wherein 80 percent of said arylene radicals are

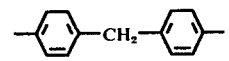

and the remainder are selected from the group consisting of

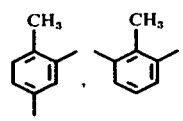

and mixtures thereof.

4. A process according to claim 1 wherein x is equal to 7.

5. A process according to claim 1 wherein said heating is carried out in the absence of solvent at a temperature of from about 160° to about 325° C.

6. A process according to claim 1 wherein said heating is carried out in the presence of an inert polar solvent at a temperature of from about 80° to about 200° C.

7. A process according to claim 6 wherein a tertiary amine catalyst is present.

8. A process according to claim 7 wherein said amine is triethylamine.

9. A process according to claim 6 wherein said solvent is tetrahydrofuran.

10. A process according to claim 6 wherein said solvent is N-methylpyrrolidone.

* * * * *